(12) United States Patent
Basso et al.

(10) Patent No.: US 8,652,108 B2
(45) Date of Patent: Feb. 18, 2014

(54) DRUG DELIVERY DEVICE AND USE OF A ROTATABLE ROLL IN A DRUG DELIVERY DEVICE

(75) Inventors: Nils Basso, Frankfurt am Main (DE); Thomas Nagel, Tharandt (DE); René Richter, Tharandt (DE); Robert Witt, Dresden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 18 days.

(21) Appl. No.: 13/319,925

(22) PCT Filed: May 20, 2010

(86) PCT No.: PCT/EP2010/056972
§ 371 (c)(1),
(2), (4) Date: Apr. 17, 2012

(87) PCT Pub. No.: WO2010/133673
PCT Pub. Date: Nov. 25, 2010

(65) Prior Publication Data
US 2012/0197212 A1      Aug. 2, 2012

(30) Foreign Application Priority Data
May 20, 2009   (EP) .................................. 09006822

(51) Int. Cl.
*A61M 5/00* (2006.01)

(52) U.S. Cl.
USPC ....................................................... 604/207

(58) Field of Classification Search
USPC .................... 604/131, 132, 134, 151, 207;
128/DIG. 12, DIG. 13; 222/100, 101, 222/401
See application file for complete search history.

(56) References Cited

U.S. PATENT DOCUMENTS

| | | | | |
|---|---|---|---|---|
| 1,207,534 | A | * | 12/1916 | Gammeter .................... 222/102 |
| 1,989,713 | A | * | 2/1935 | Smith et al. .................... 222/96 |
| 2,502,081 | A | * | 3/1950 | Flynn et al. .................... 222/98 |
| 2,549,488 | A | * | 4/1951 | Kramer .......................... 222/96 |
| 2,686,614 | A | * | 8/1954 | Geressy et al. .............. 222/102 |

(Continued)

FOREIGN PATENT DOCUMENTS

| | | |
|---|---|---|
| EP | 1923083 | 5/2008 |
| FR | 2887458 | 12/2006 |

OTHER PUBLICATIONS

European Search Report for EP App. No. 09006822, dated Dec. 17, 2009.
International Search Report for International App. No. PCT/EP2010/056972, completed Oct. 20, 2010.

*Primary Examiner* — Manuel Mendez
(74) *Attorney, Agent, or Firm* — McDonnell Boehnen Hulbert & Berghoff LLP

(57) ABSTRACT

A drug delivery device is provided which comprises a housing, a dispensing end for dispensing a drug from the drug delivery device, a flexible container for holding the drug, the flexible container comprising an outlet, the outlet being connected to the dispensing end, and a squeezing member for squeezing the flexible container, wherein, for dispensing a dose of the drug from the drug delivery device, the squeezing member and the flexible container are axially displaceable relative to one another, the squeezing member rotating with respect to the housing during the relative axial displacement and squeezing the flexible container, thereby urging the dose of the drug from the container through the outlet. Furthermore, using a rotatable roll in a drug delivery device is described.

16 Claims, 2 Drawing Sheets

(56) References Cited

U.S. PATENT DOCUMENTS

| | | | |
|---|---|---|---|
| 3,151,616 A | 10/1964 | Selfon | |
| 3,647,117 A * | 3/1972 | Hargest | 222/100 |
| 4,044,764 A * | 8/1977 | Szabo et al. | 604/134 |
| 4,850,971 A | 7/1989 | Colvin | |
| 5,211,626 A * | 5/1993 | Frank et al. | 604/65 |
| 5,728,077 A * | 3/1998 | Williams et al. | 604/246 |
| 6,416,496 B1 * | 7/2002 | Rogers et al. | 604/132 |
| 2001/0016710 A1 | 8/2001 | Nason et al. | |

* cited by examiner

DRUG DELIVERY DEVICE AND USE OF A ROTATABLE ROLL IN A DRUG DELIVERY DEVICE

CROSS REFERENCE TO RELATED APPLICATIONS

The present application is a U.S. National Phase Application pursuant to 35 U.S.C. §371 of International Application No. PCT/EP2010/056972 filed May 20, 2010, which claims priority to European Patent Application No. 09006822.2 filed on May 20, 2009. The entire disclosure contents of these applications are herewith incorporated by reference into the present application.

FIELD OF INVENTION

The present disclosure relates to a drug delivery device.

BACKGROUND

A drug delivery device is described, for example, in EP 1923083 A1.

It is an object of the present disclosure to facilitate provision of an improved drug delivery device.

This object is achieved by the subject matter of the independent claim. Advantageous refinements and embodiments are, inter alia, subject matter of dependent claims.

SUMMARY

According to an aspect, a drug delivery device comprises a housing. The drug delivery device furthermore comprises a dispensing end for dispensing a drug or medicament from the drug delivery device. The drug delivery device comprises a flexible container. The flexible container may be provided for holding the drug. The flexible container expediently comprises an outlet. The outlet may be connected to the dispensing end. The drug delivery device preferably comprises a squeezing member. The squeezing member may be provided for squeezing the flexible container. The squeezing member may be rotatable. A valve may be provided in the flow path between the outlet of the flexible container and the dispensing end. The valve may be a check valve, for example.

When dispensing and/or for dispensing a dose of the drug from the drug delivery device, the squeezing member and the flexible container may be axially displaceable relative to one another. The squeezing member may be rotatable, preferably the squeezing member rotates, with respect to the housing, in particular during the relative axial displacement. The squeezing member, in particular while rotating with respect to the housing, may squeeze the flexible container. Thereby, the dose of the drug may be urged from the container through the outlet.

Providing a flexible container for holding the drug and an external squeezing member eliminates the necessity of a rigid cartridge comprising a piston which is displaceable with respect to the cartridge for dispensing the drug from the cartridge. Accordingly, friction between piston and cartridge may be avoided and the dose accuracy may be increased. Additionally, provision of a rotatable squeezing member facilitates provision of a drug delivery device which is reliably operable with high dose accuracy.

According to an embodiment, the drug delivery device is configured such that the relative axial displacement between squeezing member and flexible container and the rotation of the squeezing member are frictionally coupled to one another.

In particular, if the squeezing member is rotated, this rotation may be converted into an axial displacement of the flexible container and the squeezing member with respect to each other. If the flexible container is axially displaced with respect to the squeezing member or if the squeezing member is axially displaced with respect to the flexible container, the respective axial displacement may be converted into rotation of the squeezing member. The relative axial displacement and/or the rotation of the squeezing member may be an externally actuated movement, e.g. driven by an external drive means, like a motor, for example.

According to an embodiment, one of the squeezing member and the flexible container is secured against axial displacement with respect to the housing. The other one of the flexible container and the squeezing member is expediently axially displaceable with respect to the housing for dispensing the dose. The one of the flexible container and the squeezing member which is not secured against axial displacement is expediently axially displaced with respect to the housing and, preferably, with respect to the other one of the flexible container and the squeezing member for dispensing of the dose.

According to an embodiment, the squeezing member is axially displaceable towards the outlet of the flexible container for dispensing the dose. Alternatively, the outlet of the flexible container may be axially displaceable towards the squeezing member for dispensing the dose.

According to an embodiment, the squeezing member comprises a rotatable roll.

According to an embodiment, the drug delivery device comprises a counter member. The counter member may provide a counter force for a force exerted by the squeezing member on the flexible container for squeezing the container. The counter member may be rotatable, e.g. a rotatable roll, with respect to the housing. Alternatively, the counter member is secured against rotation.

An intermediate space may be formed between the squeezing member and the counter member. The intermediate space may be configured for the flexible container to be guided through the intermediate space. Thereby, the flexible container may be squeezed. The flexible container may be arranged in the intermediate space during dispensing of the dose. The intermediate space and the flexible container may be axially displaced relative to one another during the relative axial displacement of the squeezing member and the flexible container.

The counter member may be secured against axial displacement with respect to at least one of or both of: squeezing member, housing.

According to an embodiment, a part of the flexible container which part holds the drug is provided rolled up onto a rotatable dispenser member, e.g. a dispenser roll, with that part being at least partially unrolled from the dispenser member during dispensing of the dose. The dispenser member may be part of a cassette, which may protect that part of the flexible container which is arranged within the cassette and contains the drug.

According to an embodiment, a part of the flexible container from which drug was displaced, in particular during dispensing of the dose, is wound on a rotatable receiving member, e.g. a receiving roll, in particular during dispensing of the dose. The receiving member and/or the dispenser member may be part of a replaceable container unit, which may be replaced when the last dose of drug was dispensed from the flexible container.

According to an embodiment, the flexible container is windable onto the squeezing member for squeezing the flexible container for dispensing the dose. In this case, there is preferably a tensioning force sustained between the flexible container and the squeezing member when the dose is dispensed. In this way, it may be avoided that a part of the flexible container which was already wound onto the squeezing member unwinds from the squeezing member.

According to an embodiment, the outlet of the flexible container is connected to the dispensing end of the device via a compensation member. The compensation member may be configured for compensating for an axial displacement of the outlet with respect to the dispensing end. Thereby, the outlet may be kept connected to the dispensing end. Fluid communication between container and outlet may thus be sustained, even if the outlet is displaced with respect to the dispensing end. In particular, the risk of the drug flow between outlet and dispensing end being interrupted on account of an accidentally opened flow circuit is reduced.

According to an embodiment, a control member, for example a valve, especially a check valve, is provided in the flow path between the outlet of the flexible container and the dispensing end. The control member may be adapted to temporarily permit and/or prevent flow of drug from the outlet of the container towards and through the dispensing end. Expediently, the control member is adapted to permit drug flow, when it is intended to dispense drug from the device.

According to an embodiment, the flexible container comprises a flexible bag. Thus, the flexible container may be non-self supporting. The flexible container may be collapsible.

An aspect of the disclosure relates to using a rotatable roll, e.g. a cylindrical roll, in a drug delivery device. The rotatable roll may be used for interacting with a flexible container, in particular with a flexible container for holding a drug. A rotatable roll may be used as a squeezing roll for squeezing the flexible container, as a dispenser roll for holding at least a part of the flexible container which is filled with the drug, or as a receiving roll for receiving at least a part of the flexible container from which drug was displaced. Of course, a respective rotatable roll may be used for one, more or all of that purposes.

A particular advantageous aspect of the disclosure relates to a drug delivery device comprising a housing, a dispensing end for dispensing a drug from the drug delivery device, a flexible container for holding the drug, the flexible container comprising an outlet, the outlet being connected to the dispensing end, and a squeezing member for squeezing the flexible container, wherein, for dispensing a dose of the drug from the drug delivery device, the squeezing member and the flexible container are axially displaceable relative to one another, the squeezing member rotating with respect to the housing during the relative axial displacement and squeezing the flexible container, thereby urging the dose of the drug from the container through the outlet.

A further particular advantageous aspect of the disclosure relates to using a rotatable roll in a drug delivery device for interacting with a flexible container as a squeezing roll for squeezing the flexible container, as a dispenser roll for holding at least a part of the flexible container which is filled with drug, or as a receiving roll for receiving at least a part of the flexible container from which drug was displaced.

Features which were described above in connection with different embodiments and aspects may, of course, be combined with one another. Further features, advantages and expediencies of the present disclosure become apparent from the description of the exemplary embodiments in conjunction with the figures.

BRIEF DESCRIPTION OF THE FIGURES

Like elements, identically acting elements and elements of the same kind may be provided with the same reference numerals throughout the figures.

DETAILED DESCRIPTION

Figure 1:
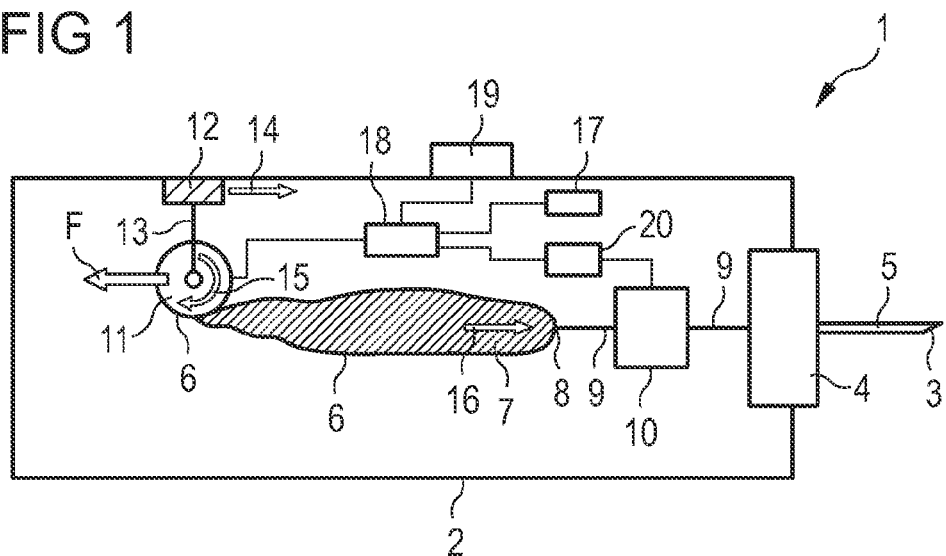
FIG. 1 shows an exemplary embodiment of a drug delivery device on the basis of a schematic sectional view.

FIG. 1 shows an exemplary embodiment of a drug delivery device on the basis of a schematic sectional view. The drug delivery device 1 comprises a housing 2. The device 1 further comprises a dispensing end 3. Drug may be dispensed from the device 1 via the dispensing end 3. The drug delivery device 1 comprises a needle unit 4. The needle unit 4 has a needle 5. An end of the needle 5 which is remote from the housing may be the dispensing end 3 of the device 1.

The housing 2 is expediently provided to protect elements of the drug delivery device which are retained or housed therein against harmful external influences. Drive and control elements of the drug delivery device 1 may be housed within housing 2.

The drug delivery device 1 comprises a flexible container 6. A drug 7 is retained within the flexible container 6. The drug 7 may comprise insulin, like a short-acting or a long-acting insulin, heparin or growth hormones, for example. The drug 7 may be or may comprise a fluid. The flexible container 6 is preferably formed non-self supporting. The flexible container 6 may be collapsible. If drug 7 is displaced from a part of the flexible container 6, that part of the container may collapse as the drug, which was previously supporting that part of the container is no more present in that part of the container 6.

The flexible container 6 has an outlet 8. The outlet 8 is connected to the dispensing end 3. Thus, fluid communication is possible between the flexible container 6 and the dispensing end 3. For this purpose, a connector 9 may be provided. Fluid drug 7 may flow from the outlet 8 through the connector 9 towards and through the dispensing end 8. The connector 9 may have two ends, with one end being connected to the outlet 8 and the other one being connected to the dispensing end 3, for example via a connection of connector 9 to needle unit 4. The connector 9 may provide for a flow path between the outlet 8 of the flexible container 6 and the dispensing end 3. The connector 9 may be or may comprise a tube, in particular a flexible tube, or a pipe.

The device 1 further comprises a flow control member 10. The flow control member 10 may be, depending on its state of operation, provided for (temporarily) preventing or permitting fluid communication between the flexible container 6 and the dispensing end 3. The flow control member 10 may be switchable between a dispensing mode and a non-dispensing mode. In the dispensing mode, fluid communication between the container outlet 8 and the dispensing end 3 is expediently permitted, preferably by an according operation of the flow control member 10. Thus, in the dispensing mode, drug 7 may flow from the container outlet 8 via the control member 10 towards and through the dispensing end 3 of the device 1. In the non-dispensing mode, i.e. when no drug should be dispensed from the device, the flow control member 10 expediently prevents flow of the drug from the container outlet 8 towards the dispensing end 3. The flow control member 10 may comprise a valve, for example. If the valve is open, flow of drug 7 from the dispensing end 3 is permitted. If the valve is closed, drug being dispensed from the device through the dispensing end or from the flexible container is prevented. The valve is preferably designed in such a manner that the pressure required to open the valve is large enough to prevent the drug from unintentionally escaping from the flexible container, which might otherwise happen owing to the effect of the gravitation. To this end the valve may be a check valve, particularly a passive check valve. If a check valve is used, the checking pressure in the reverse direction is appropriate to prevent air or body liquid from being taken in through the needle. The control member 10 may be a mechanically or electrically operable and/or controllable member.

The drug delivery device 1 further comprises a squeezing member 11. The squeezing member 11 may be configured to and expediently arranged to squeeze the flexible container 6. If the flexible container 6 is squeezed and drug 7 is displaced within the container, drug may be dispensed from the dispensing end 3 of the device, provided that the control member permits fluid communication between container 6 and dispensing end 3. The squeezing member may pressurize the drug 7 within the container 6. The pressure exerted by the squeezing member 11 on the drug 7 may result in drug being dispensed from the device 1. The squeezing member 11 may be in immediate contact with the flexible container 6, in particular with an outer wall thereof.

The squeezing member 11 is expediently rotatable with respect to the housing 2. The squeezing member 11 may be or may comprise a rotatable roll. The rotatable roll may be of cylindrical shape. The squeezing member 11 may be frictionally coupled to the flexible container 6. In particular, by means of the frictional coupling, movement of one of the flexible container 6 and the squeezing member 11 with respect to the housing may cause movement of the other one of the flexible container and the squeezing member with respect to the housing. The outer surface of the squeezing member 11 may be configured for a frictional coupling between squeezing member and flexible container 6. For example, the outer surface may comprise or be formed by a rubber material, which may result in high friction between container and squeezing member.

The squeezing member 11 may be supported by a support member 12. Support member 12 may be movable with respect to the housing 2, in particular axially displaceable with respect to the housing. Support member 12 may be displaceable with respect to the housing 2 and, in particular, with respect to the flexible container 6. Alternatively, the support member 12 may be firmly secured to the housing (not explicitly shown in FIG. 1). Of course, in this case, the squeezing member 11 may be supported by the housing 2. A separate support member 12 may then be dispensed with. If the squeezing member 11 is non-displaceable with respect to the housing 2, the flexible container is preferably displaceable with respect to the housing and, in particular, with respect to the squeezing member. The squeezing member 11 may rotate with respect to the support member 12. The squeezing member 11 may be connected to the support member 12 by a connection member 13. The squeezing member 11 is rotatable with respect to the connection member 13.

For dispensing a dose of the drug 7 from the drug delivery device 1, squeezing member 11 and flexible container 6, in particular its outlet 8, are axially displaceable with respect to each other. If the squeezing member 11 is axially displaceable with respect to the housing 2, the outlet 8 of the flexible container is expediently not axially displaceable with respect to the housing. Thus, the squeezing member 11 may be displaced towards the outlet 8 when dispensing a dose. The flexible container 6, preferably at least its outlet is preferably secured against axial displacement in this case. If the squeezing member 11 is secured against axial displacement with respect to the housing 2, the flexible container 6, and thus also the outlet 8, may be displaced with respect to the housing for dispensing the dose. Thus, the outlet 8 may be displaced towards the squeezing member 11, in this case (not explicitly shown in FIG. 1, see FIG. 2, for example). Of course, it is expedient, to arrange a compensation member in the flow path between the container outlet 8 and the dispensing end 3 for compensating for the axial movement of the flexible container in this case. A compensation member of this kind is described later on in connection with the description of FIG. 2.

Accordingly, when dispensing a dose of the drug 7, the squeezing member 11 and the flexible container 6 may be axially displaced with respect to one another. The squeezing member 11 may rotate during the relative axial displacement. While rotating and during the relative axial displacement, the squeezing member squeezes the flexible container and may thereby urge a dose of the drug from the container 6 through the outlet 8. Movement of the support member 12, which results in axial movement of the squeezing member 11 with respect to the housing 2 and the outlet of the flexible container is indicated in FIG. 1 by arrow 14.

In the embodiment shown in FIG. 1, the flexible container 6 is wound onto the squeezing member 11 for squeezing the flexible container for dispensing drug 7. The flexible container, in particular, an end thereof, may be secured to the squeezing member 11. The rotation direction of the squeezing member 11 during the dose dispensing process is indicated by arrow 15. Preferably, a drive means drives rotation of the squeezing member 11. Thereby, the flexible container 6 may be wound onto the squeezing member 11. Accordingly, the squeezing member 11 is axially displaced towards the outlet 8.

The squeezing member 11 may be adapted to rotate in one direction only when dispensing a dose. That is to say, rotation of the squeezing member 11 in another direction, in particular a direction opposite to the rotation direction during dose dispense is expediently avoided. Alternatively or additionally, it is preferred for a tension force F being present between the flexible container 6 and the squeezing member 11. Unwinding of a part of the flexible container 6 which was already wound up on the squeezing member 11 may be avoided in this way. The flexible container 6 may be kept under permanent tension, in particular before, during, and/or after dose dispense.

The relative axial displacement between squeezing member 11 and flexible container 6 and the rotation of the squeezing member may be movements coupled to one another via a frictional connection. Accordingly, if the squeezing member 11 is rotated, this rotation may be converted into an axial displacement of the flexible container 6 and the squeezing member with respect to each other. Alternatively, if the flexible container 6 is axially displaced with respect to the squeezing member 11 or vice versa, this relative axial displacement may be converted into a rotation of the squeezing member. The relative axial displacement and/or the rotation of the squeezing member may be driven, e.g. by a drive means, like a motor, for example (not explicitly shown).

The direction in which drug is displaced from the flexible container 6 when the squeezing member is rotated is indicated by arrow 16 and when squeezing member 11 and container 6 are axially displaced with respect to one another.

The actuation of the movement of squeezing member 11—rotation and/or axial displacement with respect to the housing—, the actuation of the movement of the flexible container 6—axial displacement with respect to the housing and/or with respect to the squeezing member 11—and/or the mode of operation of the control member 10 may be mechanically or electrically controlled or driven.

In the following, an electrically operable drug delivery device 1 is described in greater detail. The device 1 comprises an electrical power source 17. The power source 17 may provide the power necessary for operating the drug delivery device, in particular the operating components thereof. The power source 17 may be a battery, for example.

The device 1 furthermore comprises an electronic control unit 18. The electronic control unit 18 may control operation of components of the device 1. The control unit 18 is expediently connected to the power source 17 and may control operation of the power source. The control unit 18 may comprise an electronic processor, for example.

The device 1 further comprises an operating unit 19. Operating unit 19 may be provided for interaction with the user. Operating unit 19 may include a dose dial unit, for example a dose dial button, with which the size of a dose to be dispensed from the device may be set. The operating unit 19 may further comprise an actuation unit, for example an actuation button, with which, when actuated, the dispensing action for dispensing the previously set dose may be triggered. The operating unit 19 may also comprise a display. The display, for example an LCD, may be provided to indicate the size of the currently set dose, for example. The operating unit 19 may be the only externally accessible user-operable element of the device suitable for influencing the dispensing action. The operating unit 19 is expediently electrically conductively connected to the control unit 18 and/or to the power source 17.

The device 1 furthermore comprises a flow sensor 20, preferably an electrically operable flow sensor. The flow sensor 20 is preferably assigned and/or connected to control member 10. The flow sensor 20 may be configured to retrieve information on the amount of drug which has left the device, e.g. the amount which currently passes and/or which has already passed control member 10. Accordingly, flow sensor 20 may provide information on the amount of drug which was dispensed from the device 1. The flow sensor 20 is expediently configured to be operable to provide information about the amount of drug which has flown from device since the beginning of the dispensing action for a particular dose and before the end of that dispensing action. Flow sensor 20 may feed the respective information back to the control unit 18. Thus, flow sensor 20 may be adapted to control, whether an amount drug which corresponds to the size of the dose which was previously set by the user has been dispensed from the device. Flow sensor 20 is expediently electrically conductively connected to control unit 18 and/or power source 17. Control unit 18 may control actuation of the drive means which may be provided for rotating the squeezing member 11 and/or for axially displacing squeezing member and flexible container with respect to each other, for example an electro motor (not explicitly shown).

To set a dose, a user may dial the size of the dose, e.g. by means of the dose dial button of the operating unit 19. After the dose has been set, the user may initiate the dispensing action, for example by depressing the actuation button of the operating unit 19. The electronic control unit 18 may store the size of the set dose. A signal may be sent to the electronic control unit 18 when the actuation of the dispensing action has been triggered by the user. Thereupon, the electronic control unit 18 may actuate the rotation of the squeezing member 11 and/or the relative axial displacement of squeezing member 11 and flexible container 6. For example, electronic control unit 18 may activate rotation of the squeezing member 11 by prompting the drive means to initiate rotation of the squeezing member. The flexible container 6 may be wound onto the squeezing member 11 while it rotates. The container 6 is expediently kept under tension while it is wound up onto the squeezing member 11.

The electronic control unit 18 may prompt the flow control member 10 to switch from the non-dispensing mode to the dispensing mode after actuation of the dispensing action and, preferably, not until after needle 5 has pierced the user's skin. This may be detected by a skin piercing sensor (not explicitly shown). Due to the squeezing of the flexible container 6, drug is dispensed from the dispensing end 3 of the device 1. The flow sensor 20 may provide information about the amount of drug 7 which has left the device, in particular the amount which has passed through the control member 10, and feed this information back to the control unit 18. Accordingly, if an amount of drug 7 which corresponds to the set dose has flown from the device, the electronic control unit 18 may switch the control member 10 back into the non-dispensing mode, thereby preventing further flow of drug from the device. The electronic control unit 18 may prompt the drive means to stop rotation of the squeezing member 11 and/or to stop the relative axial displacement of squeezing member and flexible container 6.

Figure 2:
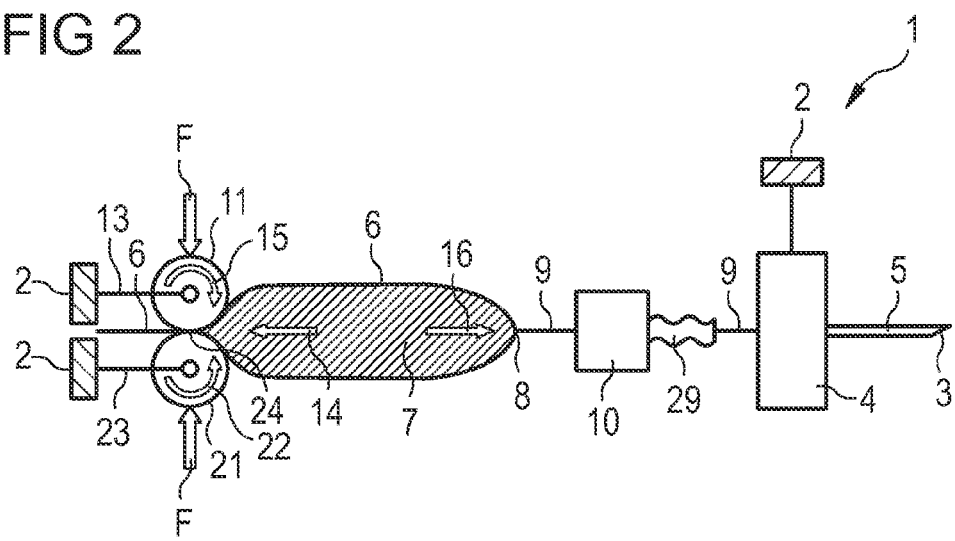
FIG. 2 shows another exemplary embodiment of the drug delivery device on the basis of a schematic sectional view.

FIG. 2 shows another exemplary embodiment of the drug delivery device on the basis of a schematic sectional view. The embodiment of FIG. 2 essentially corresponds to the one of FIG. 1. In contrast thereto, electronic components, like operating unit 19, electronic control unit 18, power source 17 and flow sensor 20 are not explicitly illustrated in FIG. 2. Likewise, housing 2 is only schematically illustrated by particular parts thereof.

In contrast to the embodiment of FIG. 1, the drug delivery device 1 shown in FIG. 2 comprises a counter member 21. The counter member may be a rotatable member, in particular a rotatable roll, e.g. a cylindrical roll. When the squeezing member 11 rotates in one direction, the counter member 21 may rotate in the opposite direction (cf. arrow 22). Counter member 21 may be connected to the housing 2, in particular secured against axial displacement with respect to the housing, for example via a connection member 23. In contrast to the embodiment depicted in FIG. 1, squeezing member 11 may be connected (immediately) to the housing 2, in particular secured against axial movement with respect to the housing.

An intermediate space 24 is formed between counter member 21 and squeezing member 11. When dispensing a dose, the flexible container 6 and the intermediate space 24 may be displaced axially relative to one another. The squeezing member 11 and the counter member 21 may be pressed against each other with a pressing force F. The flexible container 6 is guided between squeezing member 11 and counter member 21, in particular through the intermediate space 24. Thus, the force F squeezes the flexible container 6 and urges drug 7 from the container 6 through the outlet 8. In the depicted embodiment, the container 6 and, in particular, outlet 8 are displaced axially with respect to the squeezing member 11. This displacement may be externally driven by the drive means (not explicitly shown).

A compensation member 29 may be provided in the flow path between the outlet 8 of the container 6 and the dispensing end 3, in particular between the container outlet 8 and the needle unit 4. On account of the compensation member 29, the outlet 8 of the flexible container 6, and, in particular, the flexible container, may be axially displaced with respect to the needle unit without increasing the risk of a leakage in the flow path due to rapture of the connector 9. Expediently, the compensation member 29 is less rigid than connector 9 or provides for additional movement tolerances which may compensate for movement of the outlet 8 with respect to the dispensing end 3. Preferably, compensation member 29 is a flexible tube. Compensation member 29 may be provided in a curved or folded fashion, which may be sequentially straightened as the outlet 8 is sequentially moved away from the dispensing end. Compensation member 29 may, for example, initially be arranged in meander-like fashion within housing 2.

As it is illustrated, when, for dispensing a dose, the container 6 is axially displaced with respect squeezing member 11 and, in particular, with respect to counter member 21, (cf. arrow 14 indicating the relative axial movement of squeezing member 11 and flexible container 6) squeezing member 11 rotates. Also, counter member 21 rotates in the opposite direction as compared to the rotation direction of the squeezing member 11. Accordingly, the outlet 8 is moved towards squeezing member 11. Thus, drug is forced from the container outlet 8 in the direction 16. Provided that the control member 10 permits flow of drug from the dispensing end of the device, drug is dispensed from the drug delivery device 1. The compensation member 29 may be stretched or straightened during this movement. Compensation member 29 may be arranged in the flow path between control member 10 and the dispensing end 3 or in the flow path between the outlet 8 and the control member 10 (not explicitly shown).

In an alternative embodiment, which is not explicitly shown in FIG. 2, the intermediate space 24 is displaced axially with respect to the flexible container 7 in particular towards outlet 8. In this case, compensation member 29 may be dispensed with. Of course, squeezing member 11 and, in particular, counter member 21 would have to be axially displaceable with respect to the housing 2 and the flexible container 6, for example by being connected to a respective or a common movable support member.

Figure 3:
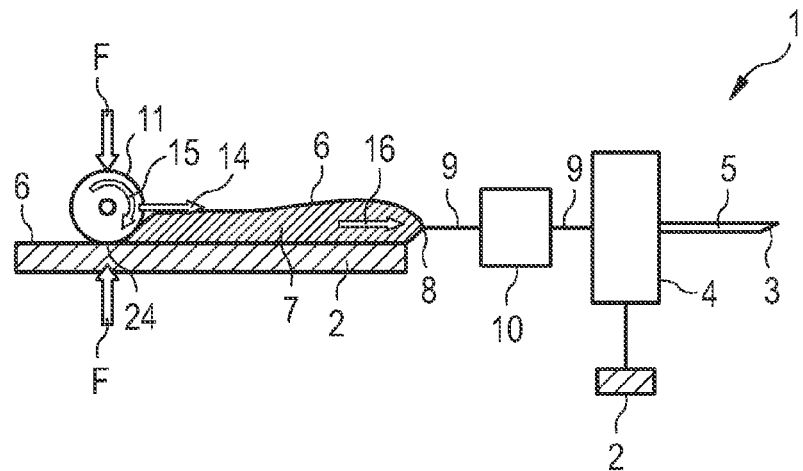
FIG. 3 shows another exemplary embodiment of a drug delivery device on the basis of a schematic sectional view.

FIG. 3 shows another exemplary embodiment of a drug delivery device 1 on the basis of a schematic sectional view. This embodiment essentially corresponds to the one depicted in FIG. 2. In contrast thereto, the intermediate space 24 is displaced towards the outlet 8 of the flexible container 6 (cf. arrow 14). The intermediate space 24 is formed between the squeezing member 11 and the housing 2 or an element which is secured against axial and rotational displacement with respect to the housing 2. Thus, no separate counter member is present. The squeezing member 11 rotates and is displaced axially with respect to the housing 2. The rotation of the squeezing member 11 may either result from the squeezing member being rotationally driven or from the frictional coupling between flexible container 7 and squeezing member 11 in combination with the squeezing member 11 being driven for an axial displacement.

Figure 4:
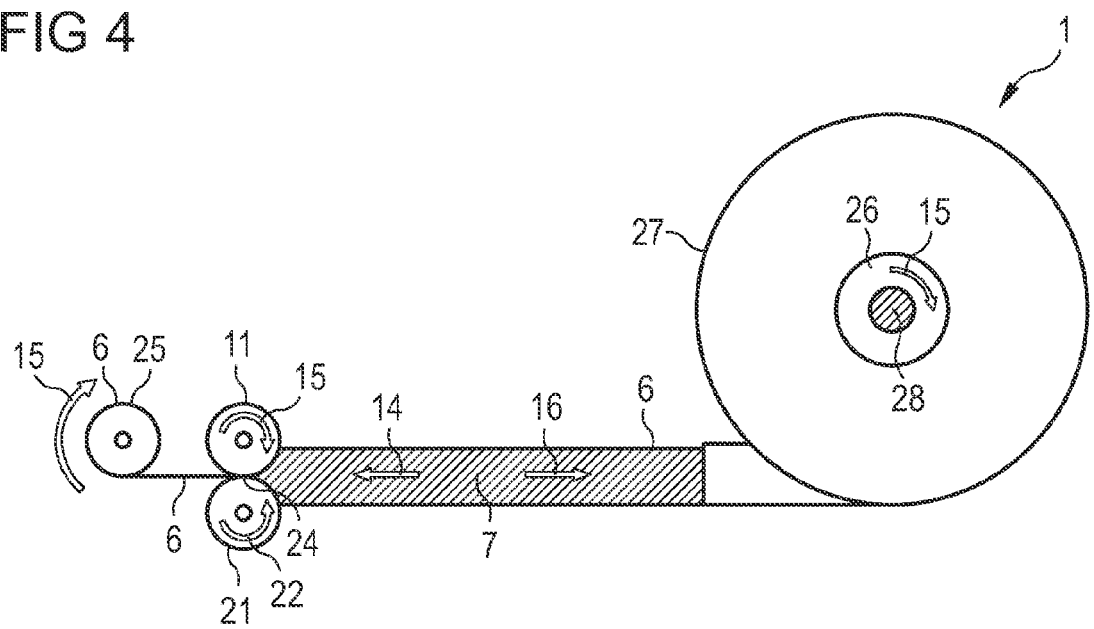
FIG. 4 shows another exemplary embodiment of a drug delivery device on the basis of a schematic sectional view.

FIG. 4 shows another exemplary embodiment of a drug delivery device 1 on the basis of a schematic sectional view. This embodiment essentially corresponds to the one depicted and described in conjunction with FIG. 2. In particular, the intermediate space 24 is formed between the squeezing member 11 and counter member 21 which may be rotatable.

The part of the flexible container, from which the drug 7 was displaced is wound up onto a rotatable receiving member 25, in particular a rotatable receiving roll, e.g. a cylindrical roll. The flexible container, in particular an end thereof, may be fixed to the receiving member 25. That part of the flexible container 6 which still contains drug may be, at least partly, provided wound up on a rotatable dispenser member 26, in particular a rotatable dispenser roll, e.g. a cylindrical roll. The flexible container 6, in particular an end thereof, may be secured to the dispenser member 26. The drug-filled container may be protected by a cassette 27, e.g. similar to a photo film protected by a film container. The rotation axes of the receiving member 25, the dispenser member 26, the squeezing member 11 and/or counter member 21 may be aligned with respect to each other, e.g. parallel. Receiving member 25, dispenser member 26 and/or squeezing member may rotate in the same direction. The drive means may drive receiving member 25 rotationally for displacing the flexible container 6 axially with respect to the squeezing member 11. Receiving member 25 and/or dispenser member 26 may be secured against axial displacement with respect to the housing.

The outlet of the flexible container (not explicitly shown) is connected to a dispensing outlet 28 of the dispenser member 26. The dispensing outlet 28 may be connected to the dispensing end (not explicitly shown). Accordingly, when being displaced from the flexible container 6, the drug may flow along the rotation axis of the dispenser member 26. The dispenser member 26 may comprise a hollow. The drug 7 may flow through the hollow towards the dispensing outlet 28. From the dispensing outlet 28, the drug 7 may flow to the dispensing end, for example via the needle unit (not explicitly shown).

A drug delivery device as proposed above has various advantages. For example, a piston which is provided in regular rigid cartridges can be dispensed with. Thus, friction between piston and container may be avoided which may, in turn, increase the dose accuracy. Also, the flexible container may be easily replaced, whereas the remaining elements of the drug delivery device, in particular the squeezing member may be re-used. The outlet 8 of the flexible container 6 may be connected to a more rigid adaptor (not explicitly shown). Adaptor and flexible container may form a container unit. The container unit may be replaced when the container has been emptied. The adaptor may serve for fluidly connecting container 6 and dispensing end 3. Additionally, flexible containers are usually lighter than regular cartridges which may be made from glass, for example. Thus, provision of a flexible container facilitates provision of a light-weighted drug delivery device. Using a rotatable roll for the various elements described above facilitates provision of a drug delivery device reliably operating and exhibiting high dose accuracy.

The drug delivery device 1 may be a stationary device or a portable device. The drug delivery device may be a pen-type device. The drug delivery device may be an injection device. Preferably, the drug delivery device is an injection pen.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

```
H-(Lys)4-des Pro36, des Pro37 Exendin-4(1-39)-NH2,

H-(Lys)5-des Pro36, des Pro37 Exendin-4(1-39)-NH2, des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39),
``` wherein the group -Lys6-NH2 may be bound to the C-terminus of the Exendin-4 derivative;
or an Exendin-4 derivative of the sequence

```
H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;
``` or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The disclosure is not restricted to the exemplary embodiments by the description on the basis of those exemplary embodiments. Rather, an invention may encompass any new feature and also any combination of features, which in particular comprises any combination of features in the patent claims and any combination of features in the exemplary embodiments, even if this combination is not explicitly specified in the patent claims or exemplary embodiments.

The invention claimed is:

1. A drug delivery device, comprising:
a housing defining an interior space,
a dispensing end for dispensing a drug from the interior of the housing,
a flexible container positioned entirely within the interior of the housing for holding the drug, where a portion of the flexible container containing the drug is stored in a dispenser, the flexible container comprising an outlet, the outlet being connected to the dispensing end, and
a squeezing member for squeezing the flexible container, wherein, for dispensing a dose of the drug from the drug delivery device, the squeezing member and the flexible container are axially displaceable relative to one another, the squeezing member rotating with respect to the housing during the relative axial displacement and squeezing the flexible container, thereby urging the dose of the drug from the container through the outlet, wherein
a valve is provided in the flow path between the outlet of the flexible container and the dispensing end.

2. The drug delivery device of claim 1, wherein the valve is a check valve.

3. The drug delivery device of claim 1, wherein the drug delivery device is configured such that the relative axial displacement between squeezing member and flexible container and the rotation of the squeezing member are frictionally coupled to one another.

4. The drug delivery device of claim 1, wherein one of the squeezing member and the flexible container is secured against axial displacement with respect to the housing for dispensing the dose.

5. The drug delivery device of claim 1, wherein the squeezing member is axially displaceable towards the outlet of the flexible container for dispensing the dose.

6. The drug delivery device of claim 1, wherein the outlet of the flexible container is axially displaceable towards the squeezing member for dispensing the dose.

7. The drug delivery device of claim 1, which further comprises a rotatable counter member, an intermediate space being formed between the squeezing member and the counter member, wherein the flexible container is arranged in the intermediate space during dispensing of the dose, the intermediate space and the flexible container being axially displaced relative to one another during the relative axial displacement of squeezing member and flexible container.

8. The drug delivery device of claim 7, wherein the counter member is secured against axial displacement with respect to at least one of or both of: squeezing member, housing.

9. The drug delivery device of claim 1, wherein the squeezing member comprises a rotatable roll.

10. The drug delivery device of claim 1, wherein the dispenser is rotatable and is configured to hold the portion of the flexible container containing the drug in a rolled up orientation with that portion of the flexible container being at least partially unrolled from the dispenser during dispensing of the dose.

11. The drug delivery device of claim 1, wherein a part of the flexible container from which drug was displaced is wound on a rotatable receiving roll during dispensing of the dose.

12. The drug delivery device of claim 1, wherein the flexible container is windable onto the squeezing member for squeezing the flexible container for dispensing the dose.

13. The drug delivery device of claim 1, wherein the outlet of the flexible container is connected to the dispensing end of the device via a compensation member, the compensation member being configured for compensating for an axial displacement of the outlet with respect to the dispensing end, thereby keeping the outlet connected to the dispensing end.

14. The drug delivery device of claim 1, wherein the flexible container comprises a flexible bag.

15. Use of a rotatable roll in a drug delivery device of claim 1
for interacting with a flexible container as a squeezing roll for squeezing the flexible container,
as a dispenser roll for holding at least a part of the flexible container which is filled with drug, or
as a receiving roll for receiving at least a part of the flexible container from which drug was displaced.

16. A drug delivery device, comprising:
a housing defining an interior space,
a dispensing end for dispensing a drug from the interior of the housing,
a flexible container positioned entirely within the interior of the housing for holding the drug, where a portion of the flexible container containing the drug is stored in a dispenser, the flexible container comprising an outlet, the outlet being connected to the dispensing end, and
a squeezing member for squeezing the flexible container, wherein, for dispensing a dose of the drug from the drug delivery device, the squeezing member and the flexible container are axially displaceable relative to one another, the squeezing member rotating with respect to the housing during the relative axial displacement and squeezing the flexible container, thereby urging the dose of the drug from the container through the outlet, wherein
a valve is provided in the flow path between the outlet of the flexible container and the dispensing end, and
the dispenser is rotatable and is configured to hold the portion of the flexible container containing the drug in a rolled up orientation with that portion of the flexible container being at least partially unrolled from the dispenser during dispensing of the dose.

* * * * *

UNITED STATES PATENT AND TRADEMARK OFFICE
CERTIFICATE OF CORRECTION

PATENT NO. : 8,652,108 B2  Page 1 of 1
APPLICATION NO. : 13/319925
DATED : February 18, 2014
INVENTOR(S) : Basso et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 165 days.

Signed and Sealed this

Twenty-ninth Day of September, 2015

Michelle K. Lee
*Director of the United States Patent and Trademark Office*